(12) United States Patent
Tategaki et al.

(10) Patent No.: US 9,737,577 B2
(45) Date of Patent: Aug. 22, 2017

(54) LACTIC ACID BACTERIUM-CONTAINING PREPARATION

(71) Applicant: Kaneka Corporation, Osaka (JP)

(72) Inventors: Airo Tategaki, Takasago (JP); Toyoaki Watanabe, Takasago (JP); Kazuya Hamada, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 14/642,796

(22) Filed: Mar. 10, 2015

(65) Prior Publication Data

US 2015/0182566 A1    Jul. 2, 2015

Related U.S. Application Data

(62) Division of application No. 12/743,485, filed as application No. PCT/JP2008/070995 on Nov. 19, 2008, now abandoned.

(30) Foreign Application Priority Data

Nov. 19, 2007  (JP) ................................ 2007-299503

(51) Int. Cl.
| | | |
|---|---|---|
| *A61K 35/74* | (2015.01) | |
| *A61K 35/747* | (2015.01) | |
| *A23K 10/18* | (2016.01) | |
| *A23L 33/135* | (2016.01) | |

(52) U.S. Cl.
CPC ............ *A61K 35/747* (2013.01); *A23K 10/18* (2016.05); *A23L 33/135* (2016.08); *A23V 2002/00* (2013.01); *A23Y 2220/00* (2013.01)

(58) Field of Classification Search
None
See application file for complete search history.

(56) References Cited

U.S. PATENT DOCUMENTS

| | | | |
|---|---|---|---|
| 2002/0037577 A1* | 3/2002 | Park et al. ............. | A61K 35/74 435/252.9 |
| 2004/0047849 A1 | 3/2004 | Hsu et al. | |
| 2010/0040735 A1 | 2/2010 | Fujiwara et al. | |

FOREIGN PATENT DOCUMENTS

| | | |
|---|---|---|
| JP | 9002959 A | 1/1997 |
| JP | 10-007577 A | 1/1998 |
| JP | 10-139674 A | 5/1998 |
| JP | 10-298083 A | 11/1998 |
| JP | 3585487 A | 6/2005 |
| JP | 2007-070249 A | 3/2007 |
| WO | WO-2006073145 A1 | 7/2006 |

OTHER PUBLICATIONS

Chauncey et al., Poster, A-100 / Sep. 1999 Supplement vol. 99 No. 9.*
Siragusa et al., Applied and Environmental Microbiology, Nov. 2007, p. 7283-7290 vol. 73, No. 22.*
The English translation of the International Preliminary Report on Patentability issued in related International Application No. PCT/JP2008/070995.
Nippon Shokuhin Kagaku Kogaku Kaishi vol. 54, No. 8, pp. 379-382 (2007).
Foreign Office Action for counterpart Japanese application 2009-542564 issued on Jun. 18, 2013.
Calcinaro et al., "Oral probiotic administration induces interleukin-10 production and prevents spontaneous autoimmune diabetes in the non-obese diabetic mouse", Diabetologia, 2005, vol. 48, No. 8, pp. 1565-1575.
Therapeutic Medicine of Recent Years, 2003, pp. 283.
Kano et al., Journal of Food Protection, vol. 65, No. 1, Jan. 1, 2002, pp. 153-160.
Mastrandrea et al., Allerg Immunol (Paris), 36(4):118-22.
Germond et al., Mol. Biol. Evol. 20(1):93-104, 2003.
Neugebauer et al., J. Dairy Sci, 88:1335-1341, 2005.
Daniel et al., Allergy 2007:62: 1237-1242.

* cited by examiner

*Primary Examiner* — Irene Marx
(74) *Attorney, Agent, or Firm* — Polsinelli PC

(57) ABSTRACT

An object of the present invention is to provide a useful composition that contains a highly safe lactic acid bacterium or a component derived from this lactic acid bacterium. The present invention relates to a composition comprising at least one lactic acid bacterium selected from the group consisting of *Lactobacillus delbrueckii* subsp. *lactis* strain KR-037 (NITE BP-395), *Lactobacillus delbrueckii* subsp. *lactis* strain KLAB-4 (NITE BP-394), and variants thereof, or comprising a component derived from the lactic acid bacterium. The composition of the present invention is useful as a preparation that has an excellent antiallergic function and also has at least one other function selected from an anti-autoimmune disease function, a diabetes-improving function, a neutral fat-lowering function, and so forth.

2 Claims, 2 Drawing Sheets

LACTIC ACID BACTERIUM-CONTAINING PREPARATION

RELATED APPLICATIONS

This application is a Divisional of co-pending application Ser. No. 12/743,485, filed on Jul. 19, 2010, which is a National Phase of PCT/JP2008/070995 filed Nov. 19, 2008, and which claims priority to Japanese Patent Application Number 2007-299503, filed on Nov. 19, 2007. The entire contents of each of application is hereby incorporated herein by reference.

TECHNICAL FIELD

The present invention relates to a preparation that contains a novel lactic acid bacterium or a component derived from this lactic acid bacterium as an active ingredient.

BACKGROUND ART

Changes in the living environment, such as the Westernization of the diet, the home environment, lack of exercise, high stress levels, and so forth, have in recent years led to a trend of annual increases in the number of individuals suffering from and at high risk for national diseases, i.e., allergic diseases and metabolic syndrome.

The number of patients with allergic diseases and particularly hay fever and atopic dermatitis is increasing annually, and therapeutic and preventive measures are also required from the standpoint of patient quality of life (QOL). The group I allergic diseases, such as hay fever and atopic dermatitis, start with the recognition of a substance introduced into the body as an allergen and subsequent induction of the production of IgE antibody. When the allergen is then reintroduced, the allergen binds to IgE antibodies that have become bound to receptor molecules on mast cells and granulocytes, which results in excessive release of chemical mediators, such as histamine and leukotriene, from the mast cells and granulocytes and causes allergy symptoms such as asthma, dermatitis, nasal discharge, and so forth.

Currently, there have been developed antiallergic agents that relieve allergy symptoms by inhibiting the release of these chemical mediators, antihistamine agents that inhibit the transmission of information by the chemical mediators to the peripheral nerves, and steroidal agents that reduce inflammation; however, side effects are seen with these drugs and at the present time there are also safety issues with regard to their methods of use and their long-term use.

In addition, the number of patients with so-called lifestyle diseases, i.e., diabetes, hyperlipidemia, hypertension, and so forth, is also following an upward course. These diseases are believed to be caused by an accumulation of undesirable lifestyles, e.g., unbalanced diet, lack of exercise, alcohol consumption, and smoking, and so forth. While dietary therapy and exercise therapy are regarded as effective methods for the treatment and prevention of these diseases, it is difficult to rigorously sustain these therapies, and therapeutic and preventive methods are thus required that are not accompanied by severe mental and physical demands.

On the other hand, fermented food products that employ lactic acid bacteria include fermented food products that have health effects, e.g., intestinal regulatory actions, preventive effects with respect to lifestyle diseases, immunostimulatory effects, and so forth, and these products have been receiving attention. For example, in the case of yogurt, the lactic acid bacteria cells used for fermentation and the milk peptides in the fermented milk are reported to exhibit health functions as described above. At the present time attention is being paid, for example, to the antiallergic functions (for example, Patent References 1 and 2: Japanese Patent Application Laid-open No. H9-2959 and Japanese Patent No. 3585487), the anti-hyperlipidemic functions (Patent Reference 3: Japanese Patent Application Laid-open No. H10-298083), and the anti-diabetic functions (Patent Reference 4: Japanese Patent Application Laid-open No. H10-7577) of lactic acid bacteria and fermented food products. Among these, the *Lactobacillus paracasei* strain KW3110 (FERM BP-08634) described in Patent Reference 2 is reported to have a particularly high antiallergic action, but it still cannot be said that this is satisfactory. In addition, lactic acid bacteria individually having multiple functions at a high level are not well known.

Patent Reference 1: Japanese Patent Application Laid-open No. H9-2959

Patent Reference 2: Japanese Patent No. 3585487

Patent Reference 3: Japanese Patent Application Laid-open No. H10-298083

Patent Reference 4: Japanese Patent Application Laid-open No. H10-7577

SUMMARY OF THE INVENTION

An object of the present invention is to provide a useful composition that contains a highly safe lactic acid bacterium or a component derived from this lactic acid bacterium. A further object is to provide a preparation that contains a lactic acid bacterium, or a component derived from this lactic acid bacterium, that has, e.g., an antiallergic function, an anti-autoimmune disease function, a diabetes-improving function, and/or a neutral fat-lowering function.

As a result of intensive investigations in order to solve the problems mentioned above, the present inventors found that a specific lactic acid bacterium belonging to *Lactobacillus delbrueckii* subsp. *lactis* has an excellent antiallergic function and also has at least one other function selected from an anti-autoimmune disease function, a diabetes-improving function, a neutral fat-lowering function, and so forth. The present invention was achieved based on this finding.

More specifically, the present invention relates to a composition comprising at least one lactic acid bacterium selected from the group consisting of *Lactobacillus delbrueckii* subsp. *lactis* strain KR-037 (NITE BP-395), *Lactobacillus delbrueckii* subsp. *lactis* strain KLAB-4 (NITE BP-394), and variants thereof, or comprising a component derived from the lactic acid bacterium.

The present invention can provide a composition that contains a highly safe lactic acid bacterium or a component derived from this lactic acid bacterium. The composition according to the present invention can be used not only as an antiallergic agent effective for preventing or improving allergies which are currently regarded as national diseases, but can also be employed as a preparation such as an anti-autoimmune disease agent, a diabetes-improving agent, and/or a neutral fat-lowering agent.

BEST MODE FOR CARRYING OUT THE INVENTION

Figure 1:
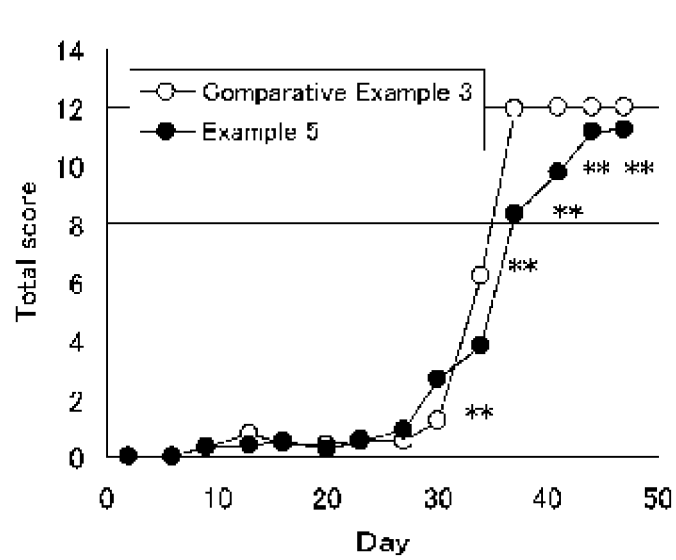
FIG. 1 shows effects of the composition of the present invention on the time course of the dermatitis score for mice with induced atopic dermatitis.

The present invention is more particularly described herebelow.

The composition of the present invention comprises at least one lactic acid bacterium selected from the group consisting of *Lactobacillus delbrueckii* subsp. *lactis* strain KR-037 (NITE BP-395), *Lactobacillus delbrueckii* subsp. *lactis* strain KLAB-4 (NITE BP-394), and variants thereof, or comprises a component derived from the lactic acid bacterium.

The *Lactobacillus delbrueckii* subsp. *lactis* strain KR-037 (also referred to below as the "KR-037 strain") in the composition of the present invention is a novel lactic acid bacterium isolated from fermented milk and belongs to *Lactobacillus delbrueckii* subsp. *lactis*. It has been deposited under accession number NITE BP-395 with the Patent Microorganisms Depositary, Incorporated Administrative Agency National Institute of Technology and Evaluation (2-5-8 Kazusakamatari, Kisarazu-shi, Chiba Prefecture, Japan) (Thereafter, the national deposit strain originally deposited on Aug. 9, 2007 was transferred to an international deposit based on the Budapest Treaty (Sep. 22, 2008).). The KR-037 strain in the present invention was identified as *Lactobacillus delbrueckii* subsp. *lactis* due to the observation of at least 90% homology with a *Lactobacillus delbrueckii* subsp. *lactis* reference strain when sequencing was performed up to 544 bases from the base at the 5' terminal of the 16S rRNA gene of the KR-037 strain.

The *Lactobacillus delbrueckii* subsp. *lactis* strain KLAB-4 (also referred to below as the "KLAB-4 strain") is also a novel lactic acid bacterium isolated from fermented milk and belongs to *Lactobacillus delbrueckii* subsp. *lactis*. It has been deposited under accession number NITE BP-394 with the Patent Microorganisms Depositary, Incorporated Administrative Agency National Institute of Technology and Evaluation (2-5-8 Kazusakamatari, Kisarazu-shi, Chiba Prefecture, Japan) (Thereafter, the national deposit strain originally deposited on Aug. 9, 2007 was transferred to an international deposit based on the Budapest Treaty (Sep. 22, 2008).). The KLAB-4 strain in the present invention was identified as *Lactobacillus delbrueckii* subsp. *lactis* due to the observation of at least 90% homology with a *Lactobacillus delbrueckii* subsp. *lactis* reference strain when sequencing was performed up to 544 bases from the base at the 5' terminal of the 16S rRNA gene of the KLAB-4 strain.

These two strains of lactic acid bacteria, as demonstrated in the examples provided below, both have an excellent antiallergic function, while the KR-037 strain also has a neutral fat-lowering function and the KLAB-4 strain also has an anti-autoimmune disease function and a diabetes-improving function.

The antiallergic function in the present invention can be evaluated, for example, as in the examples provided below, by culturing splenocytes from ovalbumin (OVA-immunized BALB/c mice in a medium supplemented with OVA and the investigational substance and measuring the cytokines (IL-12, IL-4) produced by the splenocytes. The investigational substance is considered as having an antiallergic function if, in comparison to the amount of production of cytokines IL-12 and IL-4 by splenocytes cultured in a medium lacking the investigational substance, the addition of the investigational substance results in the induction of the IL-12 production by the splenocytes and the inhibition of the IL-4 production.

The antiallergic function can also be evaluated by administering the investigational substance orally to mice and then immunizing the mice with OVA, and measuring the total IgE level in the blood from these mice. The investigational substance is considered as having an antiallergic function if the total blood IgE level in these mice is reduced in comparison to that of mice not receiving the investigational substance.

The anti-autoimmune disease function can be evaluated in accordance with the usual methods, for example, by the following method as shown in the examples provided below. First, a mouse model of collagen-induced arthritis (DBA/1J mice) is immunized with bovine type II collagen and the investigational substance is administered orally to the arthritis-induced mice. The investigational substance can be considered as having an anti-autoimmune disease function when the mice receiving the investigational substance by oral administration are observed to have a lower incidence of arthritis than mice not receiving the investigational substance. The anti-autoimmune disease efficacy can also be evaluated by observing the changes in the disease state in mice treated as described above. That is, the investigational substance can also be considered as having an anti-autoimmune disease function when, in comparison to a continual increase in the arthritis disease state score for mice not receiving the investigational substance, the disease state score for mice receiving the investigational substance orally is found to be stable so that the disease is prevented from worsening.

The diabetes-improving function (anti-diabetic function) can be evaluated, for example, as shown in the examples provided below, by measuring the time course of the blood glucose value in a sugar tolerance test in a mouse model of type 2 diabetes (KK-Ay mice) and observing a rapid decline of the blood glucose level that has been elevated by the sugar load.

The neutral fat-lowering function can be evaluated, as shown in the examples provided below, by measuring the neutral fat level in the blood of a mouse model of type 2 diabetes (KK-Ay mice) and noting a significant reduction compared to the blood neutral fat level in mice not receiving the investigational substance.

In addition to the previously described KR-037 strain and KLAB-4 strain, lactic acid bacteria that have an antiallergic function can be exemplified by *Lactobacillus delbrueckii* subsp. *lactis* strain KR-188 (accession number: NITE P-396), *Enterococcus durans* strain KR-211 (accession number: NITE P-397), and *Leuconostoc mesenteroides* subsp. *mesenteroides* strain KLAB-2 (accession number: NITE P-393).

The technical scope of the present invention encompasses not only the previously described KR-037 strain and KLAB-4 strain, but also their variants insofar as these latter have the same functions, and these variants can be incorporated in the composition of the present invention instead of the previously described KR-037 strain or KLAB-4 strain. These variants are not particularly limited and can be exemplified by variants provided by natural mutation and variants obtained by the artificial induction of mutation by known methods, for example, exposure to radiation or exposure to mutagenic substances.

Any culture medium can be used for the cultivation of the previously described KR-037 strain, KLAB-4 strain, or their variants, as long as the particular organism can grow in the culture medium. In regards to the cultivation procedure, cultivation can be carried out, for example, by test tube cultivation, flask cultivation, fermentation tank cultivation, and so forth, and there are no particular limitations thereon. For example, the MRS medium generally used for lactic acid bacteria cultivation may be used and ordinary lactic acid bacteria cultivation may be carried out under generally used conditions.

The KR-037 strain, KLAB-4 strain, or variant thereof incorporated in the composition of the present invention may be viable or dead (killed). Here, "viable" refers to the live lactic acid bacteria per se, and "dead (killed)" refers to the cells after a microbicidal treatment such as the application of heat, the application of pressure, chemical treatment, and so forth.

The technical scope of the present invention also encompasses a lactic acid bacteria-derived component from the previously described KR-037 strain, KLAB-4 strain, or their variants insofar as this component has the same functions, and this component can be incorporated in the composition of the present invention instead of the previously described KR-037 strain, KLAB-4 strain, or variants thereof. Examples of this lactic acid bacteria-derived component include a processed material (processed cell material) provided by the execution of at least one process selected from a grinding or disruption of the previously described lactic acid bacteria; conversion thereof into a liquid material by, for example, extraction; concentration; conversion into a paste; drying (spray drying, freeze drying, vacuum drying, drum drying, and so forth); and dilution, and also include a residue from the extraction of the lactic acid bacteria. The same effects as for the previously described lactic acid bacteria and variants thereof can also be obtained using these materials. Among these materials, a preferred extraction residue is, for example, a hot water extraction residue comprising the sedimented material obtained when the cells are treated with boiling water or hot water and a residue from the extraction of an extract from the cells is then collected by centrifugal separation.

The composition of the present invention, which incorporates the KR-037 strain, KLAB-4 strain, a variant of the preceding, or a lactic acid bacteria-derived component from the preceding (also referred to below simply as the "composition of the present invention"), has an excellent antiallergic effect and can therefore be used as a preparation that has an antiallergic function, i.e., as an antiallergic agent. A characteristic feature of the antiallergic agent of the present invention is that it has a very high antiallergic function. In a Th2-biased in vivo immune system, the antiallergic agent of the present invention acts to shift the immune response to antigen stimulation to a Th1-type immune response and can also limit the amount of production (antibody titer) of antigen-specific IgE. Accordingly, it can prevent or improve allergic diseases such as hay fever, atopic dermatitis, bronchial asthma, allergic rhinitis, and allergic conjunctivitis.

In addition to its antiallergic function, the composition of the present invention also has at least one selection from an anti-autoimmune disease function, an anti-diabetic function, a neutral fat-lowering function, and so forth, and thus can be used not only as an antiallergic agent, but also as an anti-autoimmune disease agent, a diabetes-improving agent, and/or a neutral fat-lowering agent.

The anti-autoimmune disease agent of the present invention can prevent the onset of an autoimmune disease, e.g., chronic rheumatoid arthritis, systemic lupus erythematosus, Hashimoto's thyroiditis, ulcerative colitis, Crohn's disease, and so forth, or can delay onset; or can inhibit the increase in the disease state score of these diseases to prevent the disease from worsening; or can improve the disease state. The diabetes-improving agent of the present invention can improve diabetes, e.g., can rapidly lower a blood glucose level that has been elevated by sugar loading so that abnormalities in sugar metabolism are improved; or can prevent the onset of diabetes. The neutral fat-lowering agent of the present invention acts to prevent or improve hyperlipidemia and abnormalities in fat metabolism by lowering the neutral fat level in the blood and controlling the neutral fat concentration in the blood.

The composition of the present invention can be used as feed (including pet food), as an animal drug, or as a drug.

With respect to the use of the composition of the present invention as feed or as an animal drug, its dosage form is not particularly limited and may be exemplified by capsules, syrups, tablets, pills, powders, granules, drinks, injectables, transfusion fluids, nose drops, eye drops, suppositories, adhesive skin patches, sprays, and so forth. With regard to formulation, production may be carried out with the suitable addition of other pharmaceutically acceptable formulating agents, for example, excipients, disintegrants, lubricants, binders, oxidation inhibitors, colorants, aggregation inhibitors, absorption promoters, dissolution auxiliaries, stabilizers, and so forth. The preparation may be mixed into a blended feed or mixed feed and may also be given suspended in drinking water. Or, the composition of the present invention may be mixed as such into a feed. In these cases, the composition of the present invention is given a single time or divided into a plurality of times so as to enable the intake, regardless of the animal species, of preferably 0.01 to 1000 mg/kg body weight per day and more preferably 0.1 to 30 mg/kg body weight per day as the lactic acid bacteria or lactic acid bacteria-derived component.

With respect to the use of the composition of the present invention as a drug, its dosage form is not particularly limited and may be exemplified by capsules, syrups, tablets, pills, powders, granules, drinks, injectables, transfusion fluids, nose drops, eye drops, suppositories, adhesive skin patches, sprays, and so forth. With regard to formulation, production may be carried out with the suitable addition of other pharmaceutically acceptable formulating agents, for example, excipients, disintegrants, lubricants, binders, oxidation inhibitors, colorants, aggregation inhibitors, absorption promoters, dissolution auxiliaries, stabilizers, and so forth. With regard to the dosage of the composition of the present invention in this case, it is administered a single time or divided into a plurality of times so as to enable the intake of preferably 0.1 to 1000 mg/kg body weight per day per person for adults and more preferably 10 to 300 mg/kg body weight per day per person for adults as the lactic acid bacteria or lactic acid bacteria-derived component.

The composition of the present invention can also be consumed on an everyday basis as a food. The form of the food that contains the composition of the present invention is not particularly limited and can be exemplified by ordinary foods, e.g., edible oil and fat compositions, cooking oils, spray oils, butters, margarines, shortenings, whipping creams, condensed milks, whiteners, dressings, pickle liquids, breads, cakes, pies, cookies, Japanese confections, snack confections, fried confections, chocolate and chocolate confections, rice confections, rouxs, sauces, bastes, toppings, iced desserts, noodles, bakery mixes, fried foods, processed meat products, other processed food products such as tofu and konjac food products, fish paste products, frozen foods (e.g., frozen entrees, frozen livestock food products, frozen agricultural foods, and so forth), cooked rice, jams, cheeses, cheese foods, imitation cheese products, gums, candies, fermented milk products, canned goods, beverages, and so forth; and also by foods with health claims, e.g., foods for specified health uses and foods with nutrient function claims, in supplement form, e.g., capsules, tablets, and so forth, and by functional foods such as health foods and dietary supplements. In the case of these functional foods and supplements, the representation can also be made that the product can be used for the prevention or improvement of allergy symptoms. There is no particular limitation on the content of the lactic acid bacteria or lactic acid bacteria-derived component when the composition of the present invention is made into a food, but, for example, the lactic acid bacteria or lactic acid bacteria-derived component can be incorporated so as to constitute 0.00001 to 100% by weight of the food, preferably 0.001 to 50% by weight, and more preferably 0.1 to 30% by weight.

Through its administration to a subject, the composition of the present invention inhibits the production of IL-4 and promotes the production of IL-12 and as a consequence can shift a Th2-biased in vivo immunity to a Th1-type immune response; it also restrains the amount of antibody-specific IgE production. As a consequence, the composition of the present invention can control or improve allergy symptoms and can prevent or improve allergic diseases such as atopic dermatitis. Thus, another embodiment of the present invention is a method of treating an allergic disease, in which the composition of the present invention is administered to a subject. The subject in this case is not particularly limited, but can be exemplified by allergic disease patients, individuals that exhibit allergy symptoms, and healthy persons or healthy animals that do not currently present allergy symptoms but are recognized as having a potential risk thereof as a result of, for example, antibody testing.

EXAMPLES

The present invention is more specifically described by the examples given below, but the present invention is in no way limited to these examples. The antiallergic function, anti-autoimmune disease function, diabetes-improving function, and neutral fat-lowering function were evaluated in the examples using the following methods.

<Evaluation of the Antiallergic Function>

Splenocytes from a mouse model of allergy (BALB/c mice) that had been immunized with OVA antigen were co-cultured with OVA and the investigational substance. The antiallergic function was evaluated based on whether IL-4 production was inhibited and IL-12 production was promoted during this co-culture.

In addition, mice receiving the investigational substance by oral administration were subjected to serial OVA immunizations and the serum IgE was measured. The antiallergic function was also evaluated based on whether the increase in the serum IgE level in mice receiving the investigational substance by oral administration was inhibited relative to an increase over time in the serum IgE level in mice not receiving the investigational substance.

<Evaluation of the Atopic Dermatitis-Improving Function>

Murine atopic dermatitis was induced by the application of picryl chloride to the right and left auricles (both inside and outside) and the back of a mouse model of atopic dermatitis (SPF male Nc/Nga mice) that received the investigational substance per os, and the dermatitis score and auricular thickness were recorded. The atopic dermatitis-improving function was evaluated based on whether an inhibitory trend was seen in the increase with time in the dermatitis score and auricular thickness in mice receiving the investigational substance per os in comparison to an increase over time in the dermatitis score and auricular thickness in mice not receiving the investigational substance.

<Evaluation of the Anti-Autoimmune Disease Function>

A mouse model of collagen-induced arthritis (DBA/1J mice) was immunized with bovine type II collagen; the investigational substance was administered orally to the arthritis-induced mice; and the arthritis incidence was recorded after 40 to 45 days. The evaluation was based on whether the incidence of arthritis was lowered by the oral administration of the investigational substance in comparison to the 100% incidence of arthritis generally seen in the collagen-induced arthritis mouse model after 40 to 45 days. The anti-autoimmune disease function was also evaluated by observation of the changes with time in the disease state score in these mice.

<Evaluation of the Diabetes-Improving Function>

The diabetes-improving function was evaluated by measuring the time course of the blood glucose value in a sugar tolerance test in a mouse model of type 2 diabetes (KK-Ay mice). More specifically, the diabetes-improving function was evaluated based on whether the blood glucose level elevated by the sugar tolerance test was thereafter rapidly lowered in mice that had received the investigational substance per os in comparison to a slow decline over time of the blood glucose level elevated by the sugar tolerance test in mice that had received water per os instead of the investigational substance.

<Evaluation of the Neutral Fat-Lowering Function>

The neutral fat-lowering function was evaluated by measuring the neutral fat level in the blood of a mouse model of type 2 diabetes (KK-Ay mice). More specifically, the neutral fat-lowering function was evaluated based on whether the neutral fat level in the blood of mice receiving the investigational substance per os was significantly reduced in comparison to the neutral fat level in the blood of mice receiving water per os instead of the investigational substance.

Production Examples 1 to 5

Production of Each Lactic Acid Bacterium

The lactic acid bacteria listed in Table 1 (Production Example 1: *Lactobacillus delbrueckii* subsp. *lactis* strain KR-037 (NITE BP-395), Production Example 2: *Lactobacillus delbrueckii* subsp. *lactis* strain KLAB-4 (NITE BP-394), Production Example 3: *Lactobacillus delbrueckii* subsp. *lactis* strain KR-188 (NITE P-396), Production Example 4: *Enterococcus durans* strain KR-211 (NITE P-397), Production Example 5: *Leuconostoc mesenteroides* subsp. *mesenteroides* strain KLAB-2 (NITE P-393)) were each cultured for 48 hours in MRS medium (prepared by dissolving 52 g MRS bouillon (Kanto Chemical Co., Inc.) in 1 L water and sterilizing the mixture by autoclaving for 15 minutes at 121° C.). After cultivation, the lactic acid bacteria cells were washed 3 times with sterilized distilled water and then freeze dried to yield freeze-dried cells of each of the lactic acid bacteria strains.

Lactic acid bacteria suspensions 1 to 5 were prepared by suspending the freeze-dried cells at 1 mg/mL in PBS(−) (trade name: Phosphate Buffer Saline, from Sigma); sterilizing the suspension for 10 minutes on a boiling water bath; thereafter obtaining a residue by centrifugal separation; and resuspending the residue in PBS(−).

Examples 1 and 2 and Reference Examples 1 to 3

Measurement of the Antiallergic Function of Lactic Acid Bacteria Groups by In Vitro Testing Five-week-old female BALB/c mice were used in this experiment after acclimation onsite for one week. To prepare the mouse model of allergy, 100 µg OVA and 2 mg aluminum hydroxide gel were mixed and brought to 200 µL with physiological saline to provide an antigen solution, and the BALB/c mice were subjected to intraperitoneal immunization with this antigen solution (primary immunization); intraperitoneal immunization was performed again with the same amount of antigen solution after one week (secondary immunization). One week after the secondary immunization, the OVA-specific IgE antibody titer was measured by ELISA in order to check the antibody titer. The splenocytes were prepared from mice that demonstrated a rise in antibody titer (allergy mouse model) and were then suspended in RPMI 1640 medium (trade name: RPMI 1640, from Sigma) containing 10% fetal bovine serum to give $2.0 \times 10^6$ cells/mL, and OVA (1 mg/mL) for antigen stimulation and one of lactic acid bacteria suspensions 1 to 5 (1 µg/mL) as shown in Table 1 were each added. The splenocytes were then cultured for 7 days in a 5% $CO_2$ incubator at 37° C., and after cultivation the supernatant was collected and the IL-4 and IL-12 present in the supernatant were measured by ELISA (product name: Quantikine, R&D Systems); this measured value was used as the value in the evaluation. These results are shown in Table 1.

TABLE 1

| | Lactic acid bacteria strain added | (Unit: pg/ml) IL-4 | IL-12 |
|---|---|---|---|
| Example 1 (Lactic acid bacteria suspension 1) | *Lactobacillus delbrueckii* subsp. *lactis* KR-037 (Accession No.: NITE BP-395) | 198.3 | 339.1 |
| Example 2 (Lactic acid bacteria suspension 2) | *Lactobacillus delbrueckii* subsp. *lactis* KLAB-4 (Accession No.: NITE BP-394) | 274.4 | 78.8 |
| Reference Example 1 (Lactic acid bacteria suspension 3) | *Lactobacillus delbrueckii* subsp. *lactis* KR-188 (Accession No.: NITE P-396) | 73.9 | 334.0 |
| Reference Example 2 (Lactic acid bacteria suspension 4) | *Enterococcus durans* KR-211 (Accession No.: NITE P-397) | 105.6 | 306.6 |
| Reference Example 3 (Lactic acid bacteria suspension 5) | *Leuconostoc mesenteroides* subsp. *mesenteroides* KLAB-2 (Accession No.: NITE P-393) | 39.6 | 356.5 |
| Comparative Example 1 | — | 3584.9 | 0.0 |
| Reference Example 4 | (Immunostimulant: Picibanil) 1) | 434.5 | 253.1 |
| Reference Example 5 | *Lactobacillus casei* L14 2) | 313.4 | 172.8 |

1) Chugai Pharmaceutical Co., Ltd., not lactic acid bacterium
2) Same as *lactobacillus paracasei* KW3110 (FERM BP-08634), identified by Japan Dairy Technical Association Comparative Example 1

Measurement of the Antiallergic Function of Lactic Acid Bacteria Groups by In Vitro Testing As a negative control, the antiallergic function was measured as in Examples 1 and 2, but in this case using PBS (−) instead of adding the lactic acid bacteria suspension. The results are shown in Table 1.

Reference Example 4

Measurement of the Antiallergic Function of Lactic Acid Bacteria Groups by In Vitro Testing As a positive control, the antiallergic function was measured as in Examples 1 and 2, but in this case, instead of adding the lactic acid bacteria suspension, 1 µg/mL of the immunostimulant Picibanil (Chugai Pharmaceutical Co., Ltd.), which has a Th1-activating action, was used. The results are shown in Table 1.

Reference Example 5

Measurement of the Antiallergic Function of Lactic Acid Bacteria Groups by In Vitro Testing For comparison with Japanese Patent No. 3585487, a lactic acid bacteria suspension as a positive control using lactic acid bacteria was prepared in the same manner as in Production Examples 1 to 5 using *Lactobacillus casei* strain L14 (Japan Dairy Technical Association, identical to *Lactobacillus paracasei* KW3110, FERM BP-08634), a lactic acid bacterium regarded as having an antiallergic activity, in place of the lactic acid bacteria used in Production Examples 1 to 5. The antiallergic function was then measured using the same conditions as in Examples 1 and 2. The results are shown in Table 1.

Table 1 shows the amount of IL-4 production and the amount of IL-12 production for the co-culture of the lactic acid bacteria and OVA with splenocytes from an allergy mouse model. In Comparative Example 1, which lacked the addition of lactic acid bacteria, IL-4 production was induced in the OVA-stimulated splenocytes of allergy mouse model, while IL-12 production was below the detection limit, and a strong Th2-type immune response was thus shown. In contrast, in Reference Example 4, which used Picibanil, IL-4 production was inhibited and IL-12 production was induced in the OVA-stimulated splenocytes of allergy mouse model, and a Th1-type immune response was thus shown. In addition, in Reference Example 5, which used *Lactobacillus casei* strain L14, a Th1-type immune response was seen as in Reference Example 4. The inhibition of IL-4 production and the induction of IL-12 production were also seen in Examples 1 and 2 and Reference Examples 1 to 3. In particular, the results in Example 1 demonstrated that a strong antiallergic activity with induction of a Th1-type immune response was seen for the KR-037 strain; moreover, a high level of antiallergic activity was demonstrated from the fact that the IL-12 production was activated by about twofold and the IL-4 production was inhibited to about two-thirds relative to the lactic acid bacterium of Reference Example 5. Otherwise, the KLAB-4 strain, as shown by the results of Example 2, while weakly inducing IL-12 production activity, provided a stronger inhibitory activity on IL-4 production than the lactic acid bacterium of Reference Example 5, which suggested the possibility of a strong antiallergic function.

Example 3

Measurement of the Antiallergic Function of a Preparation by In Vivo Testing

A lactic acid bacteria preparation was first produced by thoroughly mixing in advance 0.05 parts by weight of the freeze-dried KR-037 strain cells that had been produced in Production Example 1 with 0.45 parts by weight of an excipient (trade name: Pinedex #2, from Matsutani Chemical Industry Co., Ltd.). 0.5 Parts by weight of the produced lactic acid bacteria preparation was mixed with 99.5 parts by weight of a powdered mouse feed (product name: CE-2, from Oriental Yeast Co., Ltd.) to provide a lactic acid bacteria preparation-supplemented feed that contained 0.5% by weight of the lactic acid bacteria preparation.

Five-week-old female BALB/c mice (from Charles River Japan) were acclimated onsite for one week, after which administration of the lactic acid bacteria preparation-supplemented feed was started (ad libitum ingestion of an average of approximately 15 mg/day as the lactic acid bacteria preparation). Intraperitoneal immunization was performed with an antigen solution—prepared by mixing 100 μg OVA with 2 mg aluminum hydroxide gel and bringing the mixture to 200 μL with physiological saline—one week (Day 7) after the start day. Immunization with the OVA antigen solution was similarly performed after 2 weeks (Day 14), after 4 weeks (Day 28), after 6 weeks (Day 42), and after 8 weeks (Day 56). In order to measure the total IgE level in the blood, blood was collected from the mouse jugular vein after 3 weeks (Day 21), after 5 weeks (Day 35), after 7 weeks (Day 49), and after 9 weeks (Day 63). The serum was collected by centrifugal separation of the collected blood, and the total IgE level in the serum was measured using a "Yamasa" IgE/EIA Kit (from the Yamasa Corporation). The individual measured values are given in Table 2.

Comparative Example 2

Measurement of the Antiallergic Function of a Preparation by In Vivo Testing

The total IgE level in the collected serum was measured as in Example 3, but in this case using a powdered mouse feed (product name: CE-2, from Oriental Yeast Co., Ltd.) that had not been supplemented with the lactic acid bacteria preparation in place of the lactic acid bacteria preparation-supplemented feed. The individual measured values are shown in Table 2.

Reference Example 9

Measurement of the Antiallergic Function of a Preparation by In Vivo Testing

For comparison with Japanese Patent No. 3585487, the total IgE level in the collected serum was measured as in Example 3, but in this case using, as the lactic acid bacteria preparation-supplemented feed, a lactic acid bacteria-supplemented feed provided by mixing 99.925 parts by weight of the powdered mouse feed with 0.075 parts by weight of a health supplement comprising *Lactobacillus paracasei* KW3110 (product name: Noale Capsule, from Kirin Yakult Nextstage Co., Ltd.). The individual measured values are shown in Table 2.

TABLE 2

|  | Lactic acid bacteria added to feed | Day 0 | Day 21 | Day 35 | Day 49 | (Unit: ng/ml) Day 63 |
|---|---|---|---|---|---|---|
| Example 3 | *Lactobacillus delbrueckii* subsp. *lactis* KR-037 (Accession No.: NITE BP-395) | 0 | 147 | 450 | 510 | 547 * |
| Example 4 | *Lactobacillus delbrueckii* subsp. *lactis* KLAB-4 (Accession No.: NITE BP-394) | 0 | 207 | 732 | 890 | 994 |
| Reference Example 6 | *Lactobacillus delbrueckii* subsp. *lactis* KR-188 (Accession No.: NITE P-396) | 0 | 161 | 434 | 695 | 637 * |
| Reference Example 7 | *Enterococcus durans* KR-211 (Accession No.: NITE P-397) | 0 | 124 | 293 | 509 | 720 * |
| Reference Example 8 | *Leuconostoc mesenteroides* subsp. *mesenteroides* KLAB-2 (Accession No.: NITE P-393) | 0 | 155 | 561 | 784 | 790 * |
| Comparative Example 2 | — | 0 | 172 | 773 | 1105 | 1443 |
| Reference Example 9 | *Lactobacillus paracasei* KW3110 (trade name: Noale Capsule, from Kirin Yakult Nextstage Co., Ltd.) | 0 | 105 | 481 | 618 | 706 * |

* indicates a significant difference from Comparative Example 2

Example 4

Measurement of the Antiallergic Function of a Preparation by In Vivo Testing

The total IgE level in the collected serum was measured as in Example 3, but in this case using the freeze-dried KLAB-4 strain cells produced in Production Example 2 in place of the freeze-dried KR-037 strain cells. The individual measured values are shown in Table 2.

Reference Examples 6 to 8

Measurement of the Antiallergic Function of a Preparation by In Vivo Testing

The total IgE level in the collected serum was measured as in Example 3, but in this case using, respectively, the freeze-dried lactic acid bacteria cells produced in Production Examples 3 to 5 in place of the freeze-dried KR-037 strain cells. The individual measured values are shown in Table 2.

It is noted that differences in the mouse body weight and total quantity of intake were not seen among the experiments in Examples 3 and 4, Comparative Example 2, and Reference Examples 6 to 9.

The results in Table 2 demonstrate the following. The total blood IgE level in the mice that received the feed according to Reference Example 9 was reduced at Day 63 in comparison to that in the control group (Comparative Example 2), in which a lactic acid bacteria preparation was not incorporated in the feed. The total blood IgE level in the mice receiving the lactic acid bacteria preparation-supplemented feed in Examples 3 and 4 and Reference Examples 6 to 8 was similarly reduced at Day 63 in comparison to that in the Comparative Example 2 control. In particular, the results in Table 2 showed that the preparation that contained the freeze-dried KR-037 strain cells of Production Example 1 was, like the preparation of Reference Example 9, a preparation that had a high antiallergic activity. The change in the total IgE level in this experiment, since it is considered to be equivalent to the change in the OVA-specific IgE level, shows that an antiallergic effect was seen for the composition of the present invention.

Example 5

Measurement of the Anti-Atopic Dermatitis Function of a Preparation by In Vivo Testing 0.33 Parts by weight of the freeze-dried KR-037 strain cells produced in Production Example 1 was first mixed with 99.67 parts by weight of a powdered mouse feed (product name: CE-2, from CLEA Japan, Inc.) to provide a lactic acid bacteria-supplemented feed that contained 0.33% by weight of the freeze-dried cells.

Figure 2:
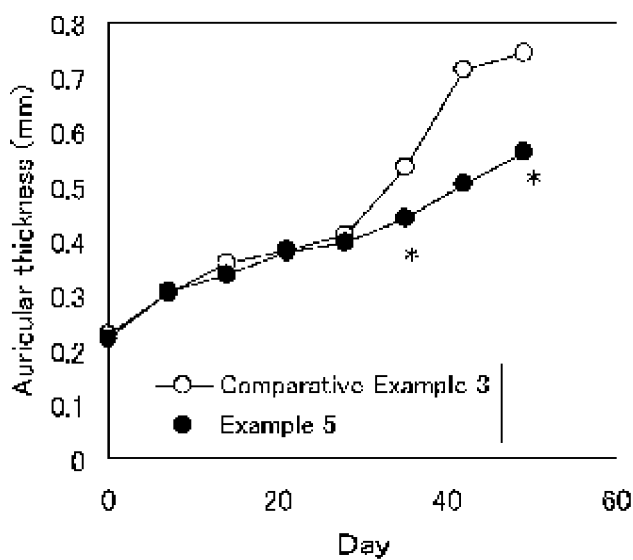
FIG. 2 shows effects of the composition of the present invention on the time course of the auricular thickness in mice with induced atopic dermatitis.

Seven-week-old SPF male Nc/Nga mice (from Charles River Japan) were acclimated onsite for one week, after which administration of the previously described lactic acid bacteria-supplemented feed was started (ad libitum ingestion of an average of approximately 10 mg/day as the preparation). One day (Day 1) after the start day, the mice were placed under isoflurane anesthesia and 150 µL of a PiCl sensitizing solution (5% (w/v) PiCl solution (solvent: ethanol/acetone=4:1)) was applied to the shaved abdomen and the footpads of the mice. The induction of atopic dermatitis was performed 4 days (Day 5) after the sensitization by applying 150 µL of a PiCl induction solution (0.8% (w/v) PiCl solution (solvent: olive oil)) to the back and the right and left auricles (both inside and outside) of the mice. This atopic dermatitis induction step was performed every week, totally 7 times. The condition of the skin was observed twice a week from the day on which sensitization was started (Day 1). Based on the clinical evaluation standards for human atopic dermatitis, five items, i.e., itching, erythema/hemorrhage, edema, excoriation/erosion, scaling/dryness, were each graded as follows: no symptoms (0 points), mild (1 point), moderate (2 points), and severe (3 points), and their sum was designated the total dermatitis score and was used for evaluation. The auricular thickness was also measured once a week using a micrometer from the test start day (Day 0). The results of measurement of the total dermatitis score are shown in FIG. 1 and the results of measurement of the auricular thickness are shown in FIG. 2.

Comparative Example 3

Measurement of the Anti-Atopic Dermatitis Function of a Preparation by In Vivo Testing The total score and auricular thickness were measured as in Example 5, but in this case using a powdered mouse feed (product name: CE-2, from CLEA Japan, Inc.) that had not been supplemented with freeze-dried lactic acid bacteria cells. The results are shown in FIGS. 1 and 2.

It is noted that differences in the mouse body weight and total quantity of intake were not seen between the experiments in Example 5 and Comparative Example 3.

The results in FIGS. 1 and 2 demonstrate the following. In the control group (Comparative Example 3), in which lactic acid bacteria were not incorporated in the feed, the total score and auricular thickness increased from the 4th atopic dermatitis induction. In contrast, the increase in the total score and the increase in the auricular thickness were both inhibited in the mice in the group (Example 5) that received feed supplemented with the freeze-dried KR-037 strain cells, and the increase was significantly inhibited from Day 34 in the case of the total score and from Day 35 in the case of the auricular thickness. These results demonstrated an anti-atopic dermatitis effect for the composition of the present invention.

Example 6

Measurement of the Anti-Autoimmune Disease Function of a Preparation by In Vivo Testing DBA/1J mice (eight week old, male, from Japan SLC, Inc.), a mouse model of collagen-induced arthritis, were used in this experiment. To induce arthritis, an arthritis induction collagen solution was prepared by dissolving bovine type II collagen (COSMO BIO Co., Ltd.) in 0.05 M acetic acid to provide 2.7 mg/mL and mixing with an equal amount, on a volumetric basis, of Freund's complete adjuvant (Wako Pure Chemical Industries, Ltd.), and arthritis onset was induced by the dorsal intradermal injection of 150 µL of this arthritis induction collagen solution (Day 0) followed, after 14 days (Day 14), by the intradermal immunization at the base of the tail with 150 µL of the same arthritis induction collagen solution as on Day 0. A lactic acid bacteria preparation was produced by mixing 40 parts by weight of the freeze-dried lactic acid bacteria (strain KLAB-4) cells produced in Production Example 2 and 60 parts by weight of an excipient (trade name: Pinedex #2, from Matsutani Chemical Industry Co., Ltd.) and was suspended in PBS(−) so as to provide 1 mg/mouse/day of the lactic acid bacteria preparation and this was forcibly administered from after 7 days (Day 7) using a plastic mouse feeding needle and a 1 mL tuberculin syringe.

The presence/absence of arthritis onset in the target mice after 44 days (Day 44), after 46 days (Day 46), and after 48 days (Day 48) was evaluated and the incidence (n=5) was determined. The results are given in Table 3.

TABLE 3

Changes in incidence in rheumatoid arthritis mouse model receiving lactic acid bacteria

|  | Lacitic acid bacteria orally administered | Dosage (cells/mouse/day) | (Incidence) Day 44 | Day 46 | Day 48 |
| --- | --- | --- | --- | --- | --- |
| Example 6 | *Lactobacillus delbrueckii* subsp. *lactis* KLAB-4 (Accession No.: NITE BP-394) | $4.0 \times 10^8$ | 0% | 20% | 20% |
| Reference Example 10 | *Leuconostoc mesenteroides* subsp. *mesenteroides* KLAB-2 (Accession No.: NITE P-393) | $4.0 \times 10^8$ | 33% | 33% | 33% |
| Comparative Example 4 | None (PBS only) | — | 66% | 100% | 100% |

Reference Example 10

Measurement of the Anti-Autoimmune Disease Function of a Preparation by In Vivo Testing The presence/absence of arthritis onset in the target mice after 44 days (Day 44), after 46 days (Day 46), and after 48 days (Day 48) was evaluated and the incidence (n=6) was determined as in Example 6, but in this case using the dried lactic acid bacteria cells produced in Production Example 5 as the lactic acid bacteria. The results are given in Table 3.

Comparative Example 4

Measurement of the Anti-Autoimmune Disease Function of a Preparation by In Vivo Testing The presence/absence of arthritis onset in the target mice after 44 days (Day 44), after 46 days (Day 46), and after 48 days (Day 48) was evaluated and the incidence (n=6) was determined as in Example 6, but in this case, instead of the administration of the lactic acid bacteria preparation, only PBS(−) was forcibly administered. The results are given in Table 3.

According to the changes over time in the incidence of arthritis in the autoimmune disease mice (Table 3), in Comparative Example 4, in which the lactic acid bacteria preparation was not given and PBS(−) alone was forcibly administered instead, swelling in the limbs was observed in 66% of the mice after 44 days (Day 44) and the onset of arthritis was observed in all the mice after 46 days (Day 46). In Reference Example 10, swelling in the limbs was observed in 33% of the mice after 44 days (Day 44), but the incidence was still 33% after 48 days (Day 48). In Example 6, on the other hand, the first onset was seen after 46 days (Day 46), for an incidence of 20%, and the incidence was still 20% after 48 days (Day 48). This demonstrated that the preparation using the KLAB-4 strain of Production Example 2 had an anti-autoimmune disease function superior to that of the lactic acid bacteria preparation of Production Example 5.

The arthritis disease state of the afflicted mice in each of the groups in Example 6, Reference Example 10, and Comparative Example 4 was evaluated based on the arthritis disease state score. The arthritis disease state score was evaluated based on grading the disease states in all the limbs (both front and rear and on both sides) on a four point scale (0: no change, 1: swelling of the toes, 2: swelling of the toes and footpads, 3: swelling of the entire limb, 4: severe swelling) and adding the scores; 1 additional point was added in the case of bone degeneration. The results are given in Table 4. The average score for the mice in Comparative Example 4 was 1.3 after 44 days (Day 44), but 4 days later, i.e., after 48 days (Day 48), had risen to 2.5. For the mice in Example 6, the disease state score was 0.2 after 46 days (Day 46), but even after 48 days (Day 48) an increase in the disease state score from this 0.2 was not seen. Based on the preceding, the preparation that used the KLAB-4 strain of Production Example 2 in particular exhibited an excellent function in that it inhibited arthritis onset and also slowed the disease progression.

TABLE 4

Changes in disease state score in mice afflicted with rheumatoid arthritis

| Lacitic acid bacteria orally administered | | (Average disease state score) | | |
|---|---|---|---|---|
| | | Day 44 | Day 46 | Day 48 |
| Example 6 | *Lactobacillus delbrueckii* subsp. *lactis* KLAB-4 (Accession No.: NITE BP-394) | 0 | 0.2 | 0.2 |
| Reference Example 10 | *Leuconostoc mesenteroides* subsp. *mesenteroides* KLAB-2 (Accession No.: NITE P-393) | 0.4 | 1.2 | 2.5 |
| Comparative Example 4 | None (PBS only) | 1.3 | 2.2 | 2.5 |

Example 7

Measurement of the Diabetes-Improving Function of a Preparation by In Vivo Testing A lactic acid bacteria preparation was first produced by mixing 0.1 parts by weight of the freeze-dried KLAB-4 strain cells that had been produced in Production Example 2 with 4.9 parts by weight of skim milk powder and 5 parts by weight of an excipient (trade name: Pinedex #2, from Matsutani Chemical Industry Co., Ltd.). 10 Parts by weight of this preparation was mixed with 90 parts by weight of a powdered mouse feed (product name: MF, from Oriental Yeast Co., Ltd.) to provide a lactic acid bacteria preparation-supplemented feed that contained 10% by weight of the lactic acid bacteria preparation with reference to the supplemented feed as a whole.

Figure 3:
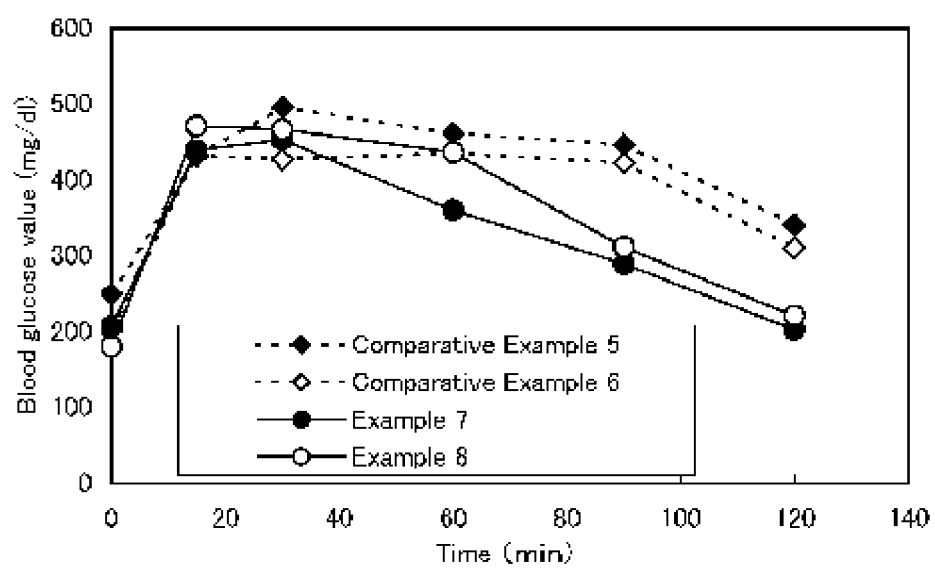
FIG. 3 shows effects of the composition of the present invention on the time course of the blood glucose value after the oral administration of an aqueous maltose solution.

Six-week-old male KK-Ay mice (from CLEA Japan, Inc.) were acclimated onsite for one week, after which administration of the aforementioned lactic acid bacteria preparation-supplemented feed was started (ad libitum ingestion of an average of approximately 150 mg/day as the preparation). At four weeks after this start day, the diabetes-improving function was evaluated on the mice using a sugar tolerance test. This evaluation was performed as follows. After an 18 hour fast, blood was collected (minute 0); 100 µL of an aqueous solution of 0.3 g/mL maltose was administered orally per mouse; blood was then collected after 15, 30, 60, 90, and 120 minutes; and the blood glucose value in each blood sample was measured using a simple blood glucose analyzer (trade name: Glutest Ace, from Sanwa Kagaku Kenkyusho Co., Ltd.). The changes over time in the blood glucose value are shown in FIG. 3.

Example 8

Measurement of the Diabetes-Improving Function of a Fermented Milk by In Vivo Testing 10% Reconstituted skim milk was sterilized at 90° C. and then cooled to 37° C.; to this was added 1% by weight of the KLAB-4 strain that had been pre-cultured in 10% reconstituted skim milk; and fermentation was then performed for 48 hours at 37° C. to produce a fermented milk. The pH of the produced fermented milk was adjusted to around 6.8 using sodium bicarbonate; this was followed by freeze drying to give a fermented milk powder.

A fermented milk preparation was produced by mixing 5 parts by weight of this KLAB-4 strain fermented milk powder and 5 parts by weight of an excipient (trade name: Pinedex #2, from Matsutani Chemical Industry Co., Ltd.). It is noted that the lactic acid bacteria concentration in this fermented milk preparation was about the same as the lactic acid bacteria concentration in the lactic acid bacteria preparation produced in Example 7. 90 Parts by weight of a powdered mouse feed (product name: MF, from Oriental Yeast Co., Ltd.) was mixed with this fermented milk preparation to provide a fermented milk preparation-supplemented feed. An evaluation was performed as in Example 7, but in this case using this fermented milk preparation-supplemented feed.

Comparative Example 5

Measurement of the Diabetes-Improving Function of a Preparation by In Vivo Testing An evaluation was performed as in Example 7, but in this case using a powdered mouse feed (product name: MF, from Oriental Yeast Co., Ltd.) that had not been supplemented with the lactic acid bacteria preparation.

Comparative Example 6

Measurement of the Diabetes-Improving Function of a Preparation by In Vivo Testing An evaluation was performed as in Example 8, but in this case using 5 parts by weight of skim milk powder and 5 parts by weight of an excipient (trade name: Pinedex #2, from Matsutani Chemical Industry Co., Ltd.) in place of the fermented milk preparation and mixing them with 90 parts by weight of a powdered mouse feed (product name: MF, from Oriental Yeast Co., Ltd.).

The results of the sugar tolerance test in the diabetes mouse model are shown in FIG. 3. In comparison to the control groups (Comparative Examples 5 and 6), in which a lactic acid bacteria preparation was not incorporated in the feed, the blood glucose levels in the mice in Examples 7 and 8 underwent a decline with time and, while presenting the maximum blood glucose levels at 20 to 40 minutes after sugar loading, had declined at 120 minutes to the levels of the blood glucose values at minute 0 (fasting blood glucose).

In the type 2 diabetes mouse model used in this experiment, a rapid decline over time of the blood glucose level elevated by the maltose load was not seen in the mice in Comparative Examples 5 and 6, while the blood glucose level in the mice in Examples 7 and 8 had declined to the fasting blood glucose at 120 minutes after the maltose load, which thus confirmed that the preparations containing freeze-dried cells or fermented milk powder of the lactic acid bacteria strain KLAB-4 had an anti-diabetic effect.

Example 9

Measurement of the Neutral Fat-Lowering Function of a Preparation by In Vivo Testing A lactic acid bacteria preparation-admixed liquid was first prepared by suspending in distilled water, so as to provide a concentration of 10% by weight, a lactic acid bacteria preparation itself prepared by mixing 33 parts of an excipient (trade name: Pinedex #2, from Matsutani Chemical Industry Co., Ltd.) with 67 parts of the freeze-dried KR-037 strain cells produced in Production Example 1.

Eight-week-old male KK-Ay mice (from CLEA Japan, Inc.) were acclimated onsite for two weeks with ad libitum intake of a mouse feed (product name: CE-2, from Oriental Yeast Co., Ltd.) and sterilized water, after which the aforementioned lactic acid bacteria preparation-admixed liquid was forcibly administered using a plastic mouse feeding needle and a 1 mL tuberculin syringe so as to provide 7.5 mL per 1 kg mouse body weight per day (forcible administration of an average of approximately 30 mg/day of the preparation per mouse).

During the period of the experiment, a mouse feed (product name: CE-2, from Oriental Yeast Co., Ltd.) and sterilized water were freely available to the mice. After two weeks of forcible administration without interruption, blood collection was performed and the neutral fat in the serum was measured using a measurement kit (Triglyceride E-Test Wako, from Wako Pure Chemical Industries, Ltd.). The measured values are shown in Table 5.

TABLE 5

|  | Neutral fat level in serum (mg/dl) |
| --- | --- |
| Example 9 | 360.1 |
| Reference Example 11 | 387.1 |
| Reference Example 12 | 477.2 |
| Reference Example 13 | 359.8 |
| Reference Example 14 | 463.3 |
| Comparative Example 7 | 596.6 |

Reference Example 11

Measurement of the Neutral Fat-Lowering Function of a Preparation by In Vivo Testing The neutral fat level in the collected serum was measured as in Example 9, but in this case using the freeze-dried lactic acid bacteria cells produced in Production Example 3 in place of the freeze-dried KR-037 strain cells. The measured values are given in Table 5.

Reference Example 12

Measurement of the Neutral Fat-Lowering Function of a Preparation by In Vivo Testing The neutral fat level in the collected serum was measured as in Example 9, but in this case using the freeze-dried lactic acid bacteria cells produced in Production Example 4 in place of the freeze-dried KR-037 strain cells. The measured values are given in Table 5.

Comparative Example 7

Measurement of the Neutral Fat-Lowering Function of a Preparation by In Vivo Testing The neutral fat level in the collected serum was measured as in Example 9, but in this case using distilled water free of a lactic acid bacteria preparation in place of the lactic acid bacteria preparation-admixed liquid. The measured values are given in Table 5.

Reference Example 13

Measurement of the Neutral Fat-Lowering Function of a Preparation by In Vivo Testing The neutral fat level in the collected serum was measured as in Example 9, but in this case the lactic acid bacteria preparation-admixed liquid was replaced with a distilled water dilution of Pioglitazone (from Takeda Pharmaceutical Co., Ltd.), which is a drug that improves insulin resistance and acts to lower the blood level of neutral fats, that had been diluted to have a concentration of 0.4% by weight. The measured values are given in Table 5.

Reference Example 14

Measurement of the Neutral Fat-Lowering Function of a Preparation by In Vivo Testing The neutral fat level in the collected serum was measured as in Example 9, but in this case replacing the lactic acid bacteria preparation-admixed liquid with a lactic acid bacteria suspension obtained by suspending a health supplement comprising *Lactobacillus paracasei* KW3110 (product name: Noale Capsule, from Kirin Yakult Nextstage Co., Ltd.) in distilled water to provide a concentration of 10% by weight. The measured values are given in Table 5.

It is noted that differences in the mouse body weight and total quantity of intake were not seen among the experiments in Example 9, Reference Examples 11 to 14, and Comparative Example 7.

The results in Table 5 demonstrate the following. The neutral fat level in the blood of the mice of Reference Example 13 (these mice received neutral fat-lowering Pioglitazone by forcible administration) was lower than the neutral fat level in the blood of the mice of Comparative Example 7 (these mice received only distillated water by forcible administration), which confirmed the neutral fat-lowering action of Pioglitazone. In addition, the same reduction in the blood neutral fat level as in the mice in Reference Example 13 occurred in the mice in Example 9 (forcible administration of a preparation produced using the KR-037 strain of Production Example 1) and the mice in Reference Example 11 (forcible administration of a preparation produced using the lactic acid bacterium of Production Example 3).

These results confirmed that the preparation produced using the lactic acid bacterium of Production Example 1 (the KR-037 strain) had a neutral fat-lowering effect and that this effect was superior to that of the other lactic acid bacteria preparations.

The invention claimed is:

1. A method of treating diabetes,
   comprising administering to a patient in need thereof at a single time or divided into a plurality of times a composition containing the lactic acid bacterium *Lactobacillus delbrueckii* subsp. *lactis* strain KLAB-4 (NITE BP-394) in an amount 0.1 to 1000 mg/kg body weight per day per person for adults in order to treat diabetes.

2. The method according to claim 1, wherein the amount of the lactic acid bacterium is 10 to 300 mg/kg body weight per day per person for adults.

* * * * *